United States Patent [19]
De La Fuente

[11] Patent Number: 6,046,463
[45] Date of Patent: *Apr. 4, 2000

[54] APPARATUS AND METHOD FOR REGULATING THE CROSS-LINKING DENSITY OF GLASS COATINGS

[75] Inventor: Fernando Javier De La Fuente, Madrid, Spain

[73] Assignee: Fuesca, S.L., Madrid, Spain

[*] Notice: This patent issued on a continued prosecution application filed under 37 CFR 1.53(d), and is subject to the twenty year patent term provisions of 35 U.S.C. 154(a)(2).

[21] Appl. No.: 08/802,528

[22] Filed: Feb. 20, 1997

Related U.S. Application Data

[63] Continuation of application No. 08/374,657, filed as application No. PCT/ES94/00056, Jun. 3, 1994, abandoned.

[30] Foreign Application Priority Data

Jun. 4, 1993 [ES] Spain ................................ 9301237

[51] Int. Cl.[7] ......................... G01B 11/06; G01N 21/88
[52] U.S. Cl. ................... 250/559.28; 250/223 B; 250/225; 356/364; 356/367; 356/369
[58] Field of Search ................. 250/225, 559.28, 250/559.27, 559.09, 559.4, 559.42, 341.1, 341.3, 341.6, 341.8, 223 B; 356/364, 366, 367, 368, 369, 370

[56] References Cited

U.S. PATENT DOCUMENTS

| | | | |
|---|---|---|---|
| 3,734,624 | 5/1973 | Cornelius | 356/369 |
| 4,015,127 | 3/1977 | Sharkins | 250/341.3 |
| 4,021,122 | 5/1977 | Krenmayr | 250/223 B |
| 4,030,836 | 6/1977 | Smith | 356/118 |
| 4,129,781 | 12/1978 | Doyle | 250/341.3 |
| 4,469,442 | 9/1984 | Reich | 356/364 |
| 4,538,912 | 9/1985 | Shaw, Jr. | 356/366 |
| 4,606,641 | 8/1986 | Yamada et al. | 356/369 |
| 4,651,011 | 3/1987 | Ors et al. | 356/368 |
| 4,826,321 | 5/1989 | Coates et al. | 356/369 |
| 4,857,738 | 8/1989 | Myers et al. | 356/370 |
| 4,904,877 | 2/1990 | Pietzsch | 250/225 |
| 5,091,320 | 2/1992 | Aspnes | 356/369 |
| 5,096,298 | 3/1992 | Isobe | 356/369 |
| 5,131,752 | 7/1992 | Yu et al. | 356/369 |
| 5,162,660 | 11/1992 | Popil | 250/225 |
| 5,170,049 | 12/1992 | De Jonge et al. | 356/369 |
| 5,210,592 | 5/1993 | Bretschneider | 250/559.42 |
| 5,245,403 | 9/1993 | Kato et al. | 356/369 |
| 5,424,536 | 6/1995 | Moriya | 250/225 |
| 5,438,415 | 8/1995 | Kazama et al. | 356/369 |

FOREIGN PATENT DOCUMENTS

| | | |
|---|---|---|
| 0144115 | 6/1985 | European Pat. Off. . |
| 0361430 | 4/1990 | European Pat. Off. . |
| 0425307 | 5/1991 | European Pat. Off. . |
| 5535229 | 3/1980 | Japan . |
| 8606943 | 10/1986 | Spain . |
| 8700641 | 1/1987 | Spain . |
| 1363029 | 12/1987 | U.S.S.R. . |

OTHER PUBLICATIONS

Born et al., *Principles of Optics*, Pergamon Press, 5th Edition, 1975, pp. 28–29 and 43.

*Primary Examiner*—John R. Lee
*Attorney, Agent, or Firm*—Ladas & Parry

[57] ABSTRACT

An apparatus and method measures and controls crosslinking treatments on a glass surface from the measurement of reflection of polarized radiation from the surface of the glass.

18 Claims, 4 Drawing Sheets

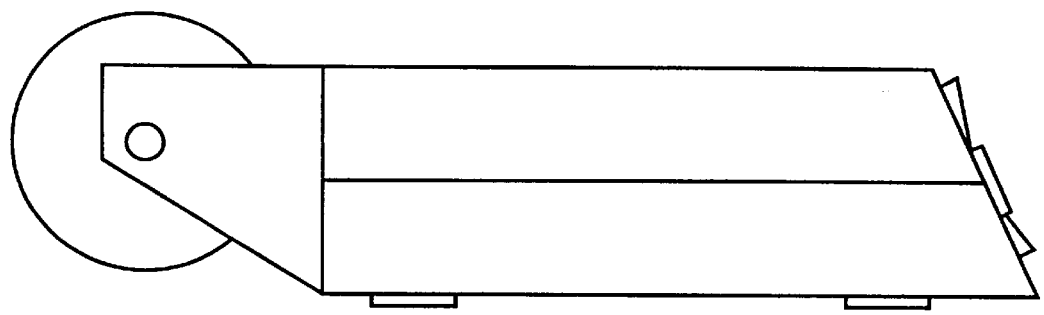
F I G. 4
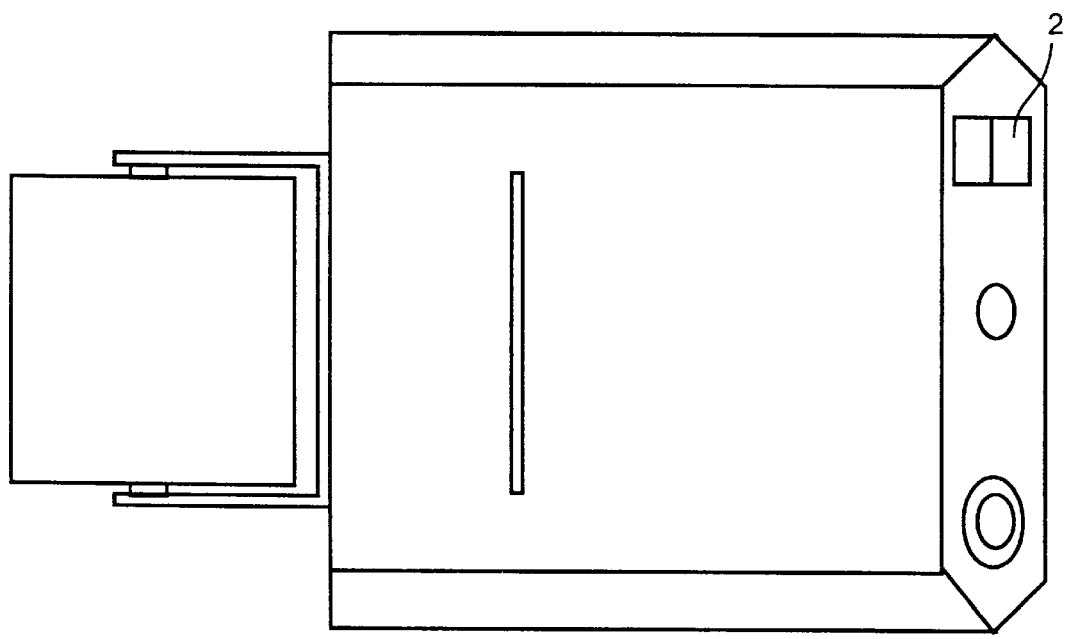
F I G. 5

APPARATUS AND METHOD FOR REGULATING THE CROSS-LINKING DENSITY OF GLASS COATINGS

This application is a continuation of application Ser. No. 08/374,657 filed on Mar. 21, 1995, now abandoned and International Application PCT/ES94/00056 filed on Jun. 3, 1994 and which designated the U.S.

DESCRIPTION

The present invention relates an apparatus and method for measurement and control of the metering out of compounds to be crosslinked in heat and cold treatments for obtaining lightened glass.

DESCRIPTION OF THE PRIOR ART

In obtaining lightened glass, a series of treatments are used, at various points on the production line, metering out products (which generally deposit tin or titanium dioxides, etc.) which, on being deposited on the surface of the glass, confer on it properties (with respect to impact resistance, resistance to pressure and to wear) which are superior to an untreated glass of the same thickness.

These treatments make it possible to obtain a glass which is 40% lighter and with up to 50% higher impact resistance, giving rise to the importance of the measurement and control of the metering out of these treatments.

Techniques are known for detection of defective glass containers by thermal shock (U.S. Pat. No. 4,733,973) or by means of variations in pressure pulses (U.S. Pat. No. 4,899,573), or techniques including those which use complex optical systems for determining shapes, volumes, cracks, presence of adhesives and geometrical defects (ESS31750, ES539594, U.S. Pat. No. 4,778,999). None of these systems have anything in common with the one described here, neither as to its purpose, nor due to the means used. The majority of these systems are not adapted to production lines, nor especially designed to detect faults in the treatments for covering crystal containers, nor give rise to the possibility of controlling the manufacturing process automatically, on the basis of the detected values. They behave in that regard as laboratory quality checks.

Currently, from the point of view of the manufacture of treated glass, the said treatment is controlled by means of the manual collection of specimens, approximately every 6 hours, determining their concentration in the laboratory and carrying out manual regulation of the speed of the metering pumps so that the metering out is maintained at the desired value. As the conditions of the treatments are not constant, these operations have to be carried out throughout the entire manufacturing process, which is continuous for 24 hours a day and all year long (except for changes in production format). All this means that actually maintaining reliability in the average quality of the manufactured product is impossible, and that faults in the quantity of treatment deposited, with the consequent loss of properties, have a considerable added cost (remelting energy, costs of manufacture, palletizing and transport etc.).

From the point of view of the user (packagers etc.) the defective material is generally discovered because the product gets scratched during handling, breaks due to slight impacts and bursts under pressure when there is a lack of treatment, while, if there is an excess of treatment, the surface of the glass takes on a metallized appearance which is inappropriate for presentation, especially of food products and drinks.

The compounds used in the treatments do not form a continuous sheet on the glass, but a non-uniform reticulated surface distribution, for which reason it is impossible to talk of measurements of the covering thickness, but rather of average concentration per unit of surface area, on which the properties which the glass acquires with these treatments will depend.

DESCRIPTION OF THE INVENTION

The apparatus and the method, which are the subject of this invention, allow reliable and automatic determination and regulation of the average quantity of treatment deposited, as well as its manual and point-like, linear or surface utilization, for use in the laboratory or on a production line.

The method proposed is based on the determination of the quantity of treatment deposited by means of the measurement of the quantity of radiation reflected by the product deposited on the surface of the glass.

If radiation is made to fall on treated glass (radiation of any wavelength and type) we will obtain a reflection due to there being a change in propagation medium (air-glass); some of this reflection will be due to the glass itself and some to the treatment product.

Since for small values of treatment the quantity reflected by the glass is quantitatively more important, and, moreover, since this is not constant as it depends above all on the surface roughness, in order to be able to obtain a reliable measurement, from the lowest values, it is necessary as far as possible to eliminate or attenuate the reflection due to the glass without affecting that due to the treatment.

This is achieved in the invention described by polarizing the radiation from the emitter in a plane which can be variable with respect to the incidence plane and to the angle of polarization of the glass. Depending on the angle formed by both vectors, total refraction occurs for the glass, or, by means of a polarization for the glass which is destructive of the radiation reflected, making use of a polarizing plate situated in front of the receiver, whereby the measurement of the reflection will be due solely to the treatment crosslinking.

The apparatus which is the subject of the invention can work equally well in one mode or the other, with total refraction at the glass or with polarization which is destructive of the reflection from the glass, solely by adapting the measurement head.

In the first mode, the head consists of a colocated emitter and receiver together forming the angle of polarization of the glass with the normal to the surface of the glass, plus a polarizing system located in front of the emitter, or a polarized radiation emitter, which allow polarization of the radiation in a polarization plane perpendicular to the incidence plane.

In the second mode, the head consists of emitter and receiver forming an equal angle with the normal to the surface of the glass, and with an adjustable polarization system in front of each of them.

In both cases the polarization systems can be substituted by emitters and receivers which are already suitably polarized.

The apparatus working according to either one of the modes described can be used in the laboratory for perimetral surface or linear point-like measurements, or on the production line for serial measurements.

The rest of the components of the apparatus of this invention is common to both modes and consists of:

1) A plinth or frame, for locating and self-centring the specimen to be measured, which makes it possible to control the angles of incidence and reflection as well as the normal to the measurement surface. This plinth also contains a cover with a pressure shoe.

The corresponding head and its suspension system which make it possible to remain in continuous contact with the surface of the glass both when at rest and when moving.

Both the head and the centring elements of the plinth are free to move, movement being adjustable in speed and direction in order furthermore to allow point readings, longitudinal readings, perimetral and spiral readings (of variable pitch according to the speed which the head is given) in a manual or automatic process, and motorized in both cases 2) The central unit which drives the emitter of the head intermittently in order to eliminate the effect of ambient radiation, with which the receiver alternately picks up an ambient signal and immediately after an ambient signal plus the measurement signal; both signals are taken to a logarithmic amplifier which amplifies the signal and sends it to a microprocessor which forms the difference between the two values and stores the result.

The visual measurement indicator, which may be pointer-type or digital (merely indicative in the case of production lines).

The metering control circuit, where the received signal is inverted, given that the correction, in terms of the metering speed of the pumps, is inversely proportional to the quantity of treatment measured.

The control circuit has been assigned an (adjustable) signal of the "standard of the treatment" value which it is desired to obtain. This signal is used so that the apparatus is regulated at the moment of switch-on and as a signal for comparison with the mean received from the microprocessor.

Depending on this comparison, another part of the control circuit corrects the treatment speed signal which the metering pump receives so that the value of the treatment is the standard one. This circuit stores the appropriate speed in memory until the next measurement and generates the corresponding signal which determines the metering speed of the pump.

Thus by successive approximations, in order to avoid abrupt jumps in the metering speed, deviations in the chosen standard value are corrected, despite the variations in the treatment and production conditions.

At the end of the selected measurement process, the arithmetic mean of all the differences (actual measurements) which are stored is obtained, and the mean obtained is downloaded onto:

3) A printer connected to the central unit, where the program of the microprocessor shows the data on:

company (assigned), production line number (assigned), date, time and treatment method; with which it is possible to produce and check graphs of production quality per line, without the necessity for continuous inspections, and to be aware when and which material produced is not within the desired values, if any.

For the apparatus intended for use in a laboratory or for determination solely of the average quality with respect to the treatment of the product which is being purchased, the metering control circuits do not come included in the central unit, and there may or may not be a connection for the printer.

The limitation on the number of checks per hour carried out by the apparatus is more dependent on whether the material checked is reincorporated into the production line or discarded, since, on average, the apparatus takes less than 30 seconds to carry out all its functions, for a reading obtained from 300 signals collected in the measurement process.

EXPLANATION OF THE FIGURES

FIG. 4: Printer side view

FIG. 5: Printer plan view

EXPLANATORY EXAMPLE 1

The apparatus has all the cables from the central unit interconnected with the plinth and the printer, the central unit and printer are plugged in to a power point, and the switch (1) of the central unit (FIG. 3) and that (2) of the printer (FIG. 5) is pressed, whereupon the entire assembly is ready to work, except for setting the clock and calendar by pressing on the corresponding buttons (3, 4 and 5—FIG. 3) situated in the central unit.

PLINTH

Figure 1:
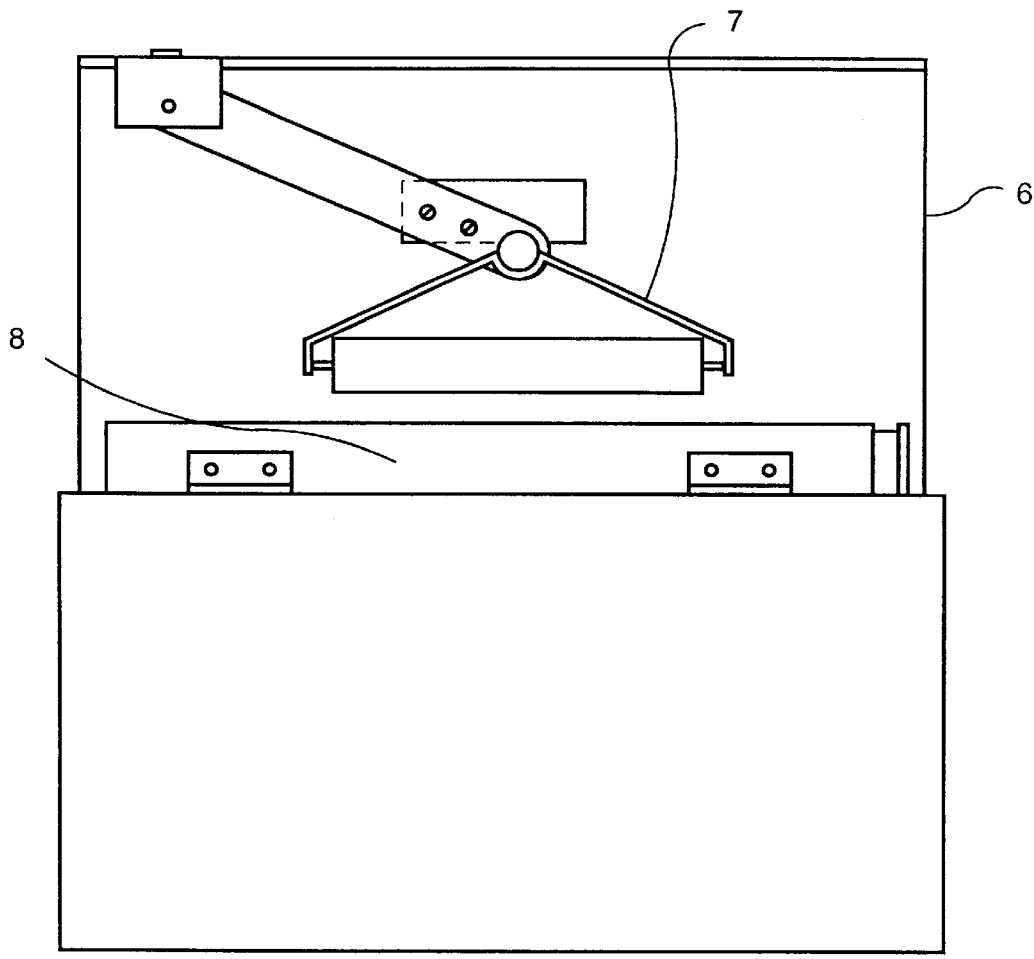
FIG. 1: Elevation view of the plinth

Given a specimen of treated glass, for example a bottle, the cover (6) of the plinth (FIG. 1) is raised, which has the pressure shoe (7) fitted to it, and it is located above the drive and centring rollers (8) situating the desired start-of-measurement region on the head (9) which will retract or advance vertically depending on the diameter of the specimen, remaining in contact with the latter. The lid (6) is lowered, whereupon the pressure shoe (7) is situated just against the bottle, centring it and pressing it against the turning rollers.

CENTRAL UNIT

It allows various possibilities to be selected:

Point average measurement

Longitudinal average measurement

Perimetral average measurement

Surface average measurement (in a spiral)

Figure 2:
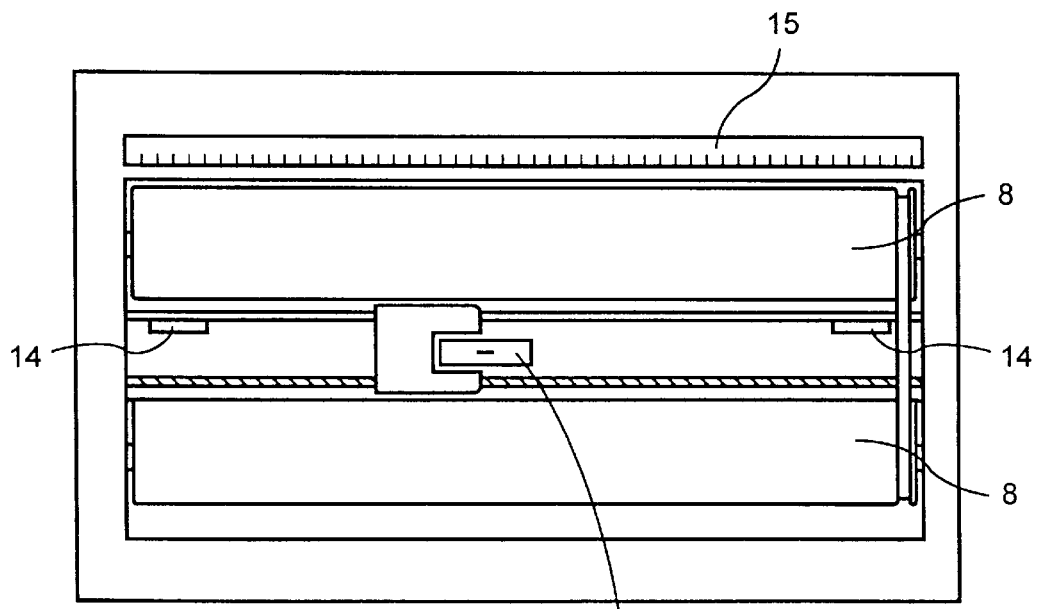
FIG. 2: Plan view of the plinth

To select one or the other, the actuation of the switch (10—FIG. 3) for turning the centring cylinders (7—FIG. 1) is combined with the push button (9—FIG. 2) for movement of the head.

If a point measurement is required to be made, the head is situated at the point to be measured by pushing on the button (1—FIG. 3) until it takes up the desired position and the red measurement button (12—FIG. 3) is pressed, whereupon the apparatus takes the measurement at the selected point and reflects it on the display (13—FIG. 3) and on the paper of the printer also indicating the date and time of the measurement. Subsequently, the head is automatically relocated in the end-of-travel rest position (14) (right or left) closest to the point at which the measurement was taken. Parallel to one of the centring rollers and of the same length, a graduated scale is fixed which makes it possible to situate the point at which the measurement was taken longitudinally. In the central unit three "high-brightness leds" are situated (16, 17 and 18—FIG. 3) indicating treatment BAND, with colours: orange (indicates treatment in high BAND), green (indicates treatment in standard BAND) and red (indicates treatment in low BAND), the latter being connected with an audible alarm.

For the longitudinal average measurement it suffices to press directly on the red measurement button (12—FIG. 3), whereby the head moves automatically taking measurements, from the rest position to the opposite end of travel. The following operations are the same as in the first case.

For the perimetral average measurement, the head is situated at the desired position by pressing on the button (11—FIG. 3) and subsequently the switch (10—FIG. 3), for turning the rollers; then the measurement is taken, pressing on the red measurement button (12—FIG. 3), with the same operations as in the first case.

For the surface average measurement (in a spiral), it is only necessary to actuate the switch (10—FIG. 3) for turning the rollers and subsequently to press the red measurement button (12—FIG. 3), whereby the head will move automatically taking a reading from the rest position to the end of travel. The following operations are the same as in the first case.

Given that the speed of advance of the head can be regulated by means of the corresponding potentiometer (20—FIG. 3), situated in the central unit, the pitch of the spiral and thereby the size of the surface area checked can be fixed at a greater or lesser size according to requirements.

EXPLANATORY EXAMPLE 2

In the case of utilization of the apparatus on a production line to control and correct the treatment; the switch (10—FIG. 3) for turning the rollers as well as the red measurement button (12—FIG. 3) are replaced by a microswitch (or a reflection photocell or barrier) combined with a time-delay relay in such a way that, when the bottle withdrawn from the conveyor belt passes through the point where the microswitch is located, it pushes the stalk of the latter giving the signal to the time-delay relay which instantaneously puts the rotation of the rollers into operation and, with a defined delay (depending on the distance left between the microswitch and the site of the plinth) initiates the measurement circuit when the pusher or gripper has situated the bottle on the drive rollers of the plinth (this pusher or gripper also substitutes for the effect of the pressure rollers and cover of the laboratory equipment). At the same time as the measurement obtained is output on the screen and on the printer, the speed of the metering equipment of the treatment is regulated, the speed of which will remain fixed until the next reading.

The same mechanical pusher or a pneumatic one withdraws the bottle from the plinth when the timer terminates its actuation time, leaving the apparatus prepared to receive a new specimen.

The specimen may be withdrawn from or returned to the production line since, throughout the measurement process, it suffers no physical or chemical variation, thereby remaining at the end of the process in the same conditions in which it was withdrawn from the production line.

Figure 3:
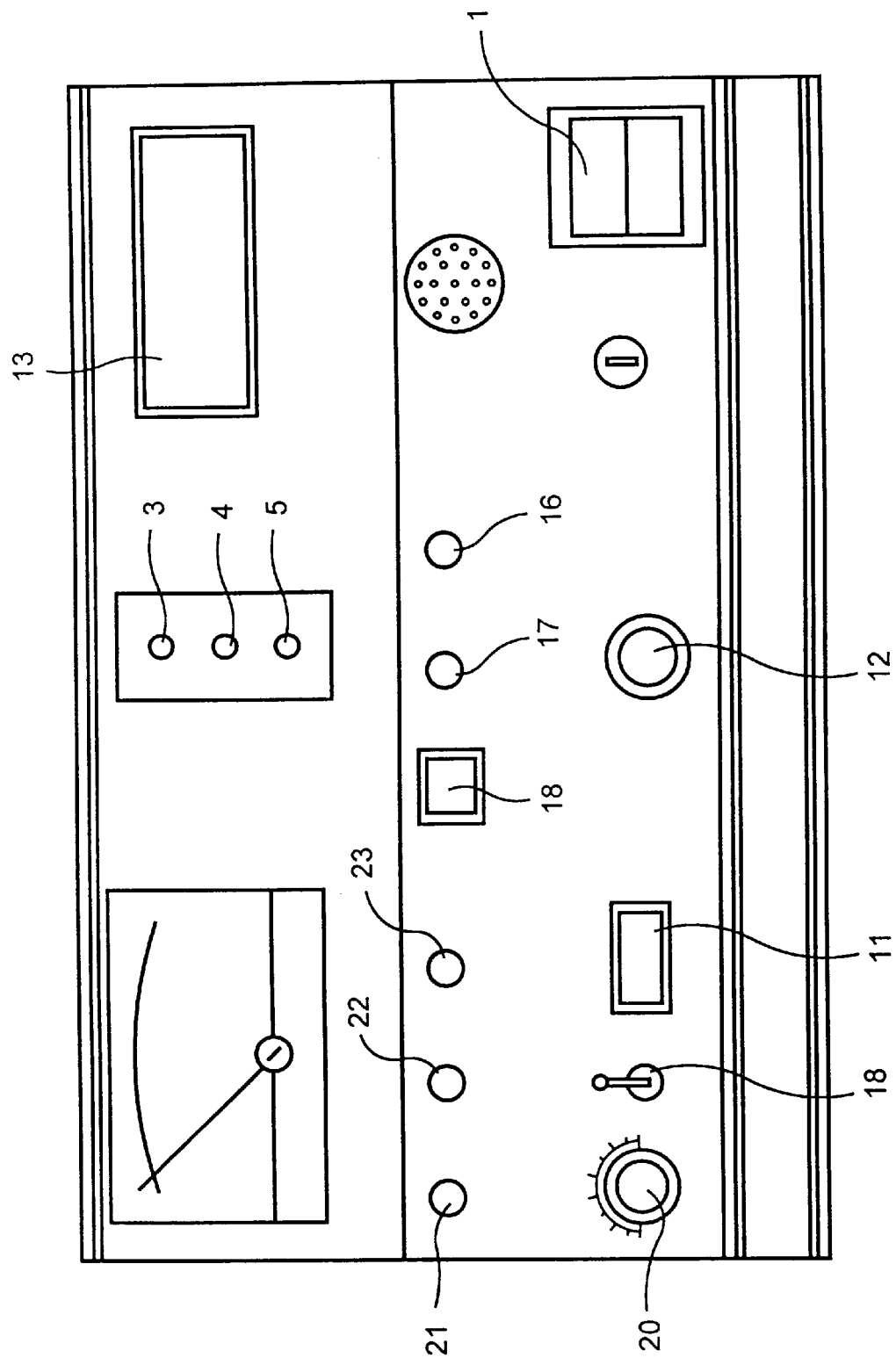
FIG. 3: Front view of the central unit
Figure 6:
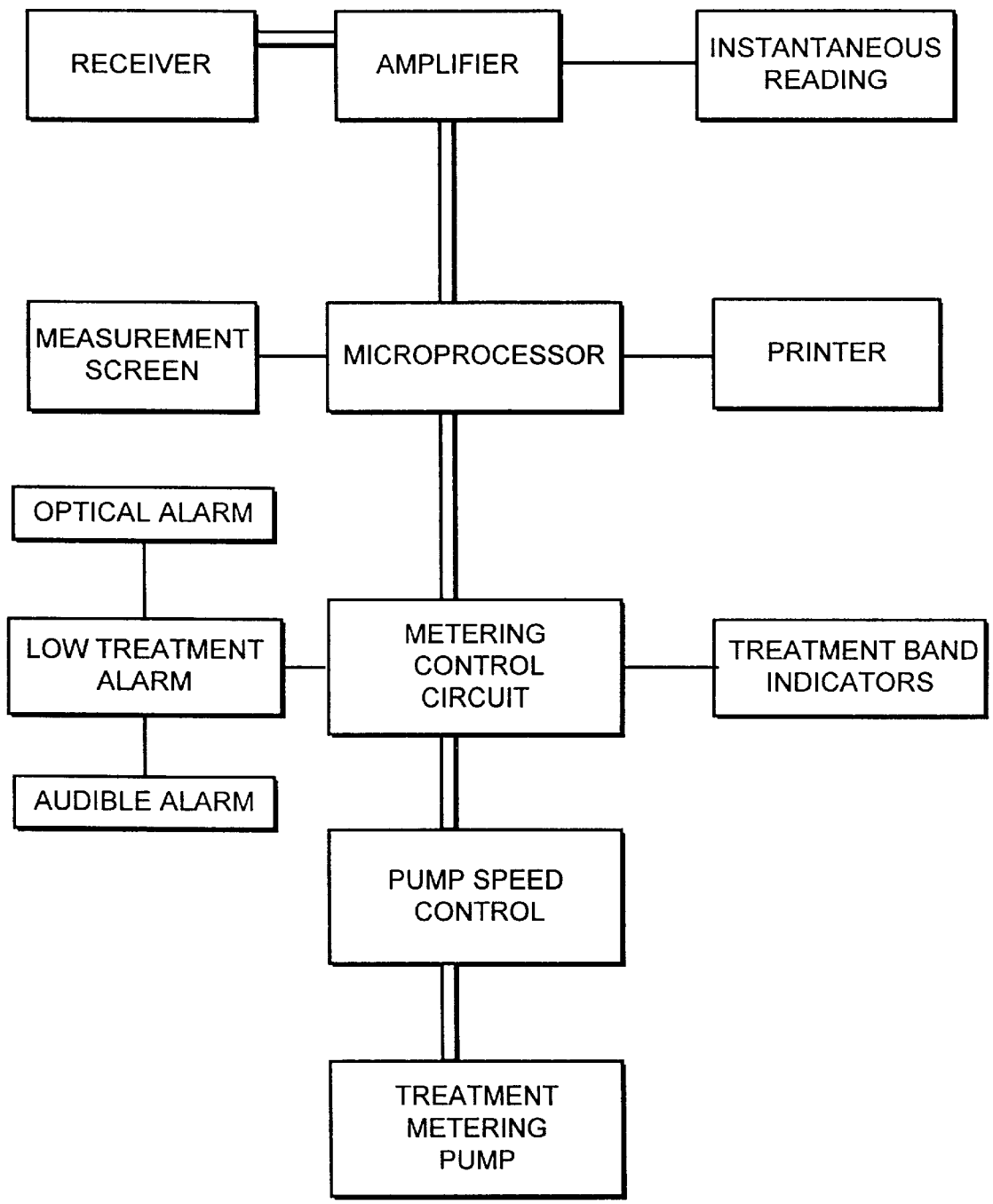
FIG. 6: Block diagram

Both the potentiometer (20—FIG. 3) for regulating the speed of the head, and the push button (11—FIG. 3) of the latter and the switch (10—FIG. 3) for turning the rollers have a corresponding operating indicator lamp (21, 22 and 23—FIG. 3).

The central unit, while the apparatus is switched on, carries out a self-check in order to detect irregularities, if there are any, in its circuits, sounding the audible alarm if appropriate. The three units of the apparatus (plinth, central unit and printer) make use of systems for protection against overcurrents (varistors and fuses of appropriate value).

I claim:

1. An apparatus for measurement and control of a concentration of a treatment deposited on a surface of a glass substrate to form a treated glass, wherein the treatment forms a non-uniform reticulated surface distribution on the surface of the glass substrate such that radiation emitted onto the treated glass is in part reflected by the treatment and in part reflected by the glass substrate, the apparatus comprising:

a plinth for positioning the treated glass;

a head for contact with the treated glass;

emitter means in the head for emitting radiation onto the treated glass that is polarized linearly in a plane parallel to an incident plane of the radiation such that, when the head is in contact with the treated glass, some of the polarized radiation is reflected by the treatment and some of the polarized radiation is incident to the glass substrate at an angle that results in nil reflection due to the glass substrate;

receiver means in the head for receiving the radiation reflected by the treatment and for determining and recording the concentration of the treatment based upon the quantity of radiation reflected by the treatment only; and processing means for processing signals from the receiver means and for controlling the treatment deposited on the surface of the glass substrate based upon the concentration determined by the receiver means.

2. An apparatus according to claim 1, wherein the plinth fixes a position of the treated glass so that the treated glass can be centered in the apparatus.

3. An apparatus according to claim 2 comprising means for motorized movement of the plinth, said movement of the plinth being adjustable in speed and duration.

4. An apparatus according to claim 1 comprising means for motorized movement of the head, the movement of the head being adjustable in speed and direction so that the measurement of the concentration of the treatment is based on point, longitudinal perimetral and spiral readings taken from the treated glass.

5. An apparatus according to claim 1, wherein the processing means feeds signals to the emitter means to cause said polarized radiation to be emitted, said signals being fed intermittently to eliminate the effect of ambient radiation.

6. An apparatus according to claim 5, wherein the receiver means alternately records a first signal which is an ambient signal and a second signal which is an ambient signal plus a measurement signal.

7. An apparatus according to claim 6, wherein the processing means comprises a logarithmic amplifier for amplifying the first and second signals recorded by the receiver means and a microprocessor coupled to the logarithmic amplifier for calculating and storing a difference between values of the first and second signals.

8. An apparatus according to claim 1, wherein the processing means comprises a metering control circuit which regulates a rate the treatment is deposited on the glass substrate based on values recorded by the receiver means.

9. An apparatus according to claim 8, wherein the metering control circuit regulates the rate by comparing a recording from the receiver means with a standard signal of treatment concentration.

10. An apparatus according to claim 1, wherein the processing means compares recordings from the receiver means with a standard value, and sends out optical or audible alarm signals or both.

11. An apparatus according to claim 1, wherein the processing means displays data measured via visual, digital or pointer indicators.

12. An apparatus according to claim 1 further comprising a printer coupled to the processing means for printing data processed by the processing means.

13. An apparatus according to claim 12, wherein the data printed by the printer is selected from the group consisting of company name, production line number, date, time, measurement of the treatment, and whether or not the concentration of the treatment is within a desired value.

14. A combination comprising the apparatus according to claim 1 and the glass substrate, the surface of the glass substrate being in contact with said head.

15. A combination according to claim 14, wherein the glass substrate has a perimetral surface.

16. A combination according to claim 15, wherein the glass substrate comprises a bottle.

17. In a method for making a product comprising a substrate of transparent or translucent glass having a crosslinked material thereon, said method comprising depositing the crosslinked material onto the glass substrate in a concentration that forms a non-uniform reticulated surface distribution of the cross-linked material on the glass substrate such that radiation emitted onto the product is in part reflected by the crosslinked material and in part reflected by the glass substrate, the improvement comprising measuring the concentration of the crosslinked material by (a) emitting onto the product radiation that is polarized linearly in a plane parallel to an incident plane of the radiation such that some of the polarized radiation is reflected by the crosslinked material and some of the polarized radiation is incident to the glass substrate at an angle that results in nil reflection due to the glass substrate, and (b) measuring the quantity of the reflected radiation whereby to ascertain the reflected radiation attributable to the concentration of the cross-linked material only.

18. A method according claim 17, further comprising regulating the concentration of the cross-linked material deposited onto the glass substrate based upon a measurement made in step (b).

\* \* \* \* \*